(12) United States Patent
Laskin et al.

(10) Patent No.: US 12,343,351 B2
(45) Date of Patent: Jul. 1, 2025

(54) PULMONARY FUNCTION TREATMENT

(71) Applicant: Rutgers, The State University of New Jersey, New Brunswick, NJ (US)

(72) Inventors: Debra L. Laskin, Basking Ridge, NJ (US); Jaclynn A. Meshanni, Hawthorne, NJ (US); Grace L. Guo, Bridgewater, NJ (US); Andrew J. Gow, Princeton, NJ (US); Jeffrey D. Laskin, Piscataway, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 94 days.

(21) Appl. No.: 18/190,680

(22) Filed: Mar. 27, 2023

(65) Prior Publication Data

US 2023/0302018 A1  Sep. 28, 2023

Related U.S. Application Data

(60) Provisional application No. 63/269,920, filed on Mar. 25, 2022.

(51) Int. Cl.
*A61K 31/575* (2006.01)
*A61P 11/00* (2006.01)

(52) U.S. Cl.
CPC ............ *A61K 31/575* (2013.01); *A61P 11/00* (2018.01)

(58) Field of Classification Search
CPC .............................. A61P 11/00; A61K 31/575
See application file for complete search history.

(56) References Cited

U.S. PATENT DOCUMENTS

9,732,116 B2 * 8/2017 Steiner ................. C07J 9/005
10,758,549 B2   9/2020 Lancaster et al.
11,273,203 B2 * 3/2022 Eichenbaum .......... A61P 39/02

FOREIGN PATENT DOCUMENTS

WO      2013192097 A1    12/2013
WO  WO-2015095386 A1 *  6/2015  ............. A61K 31/18
WO      2016176208 A1    11/2016

OTHER PUBLICATIONS

Okazaki, A., Takeda, Y., Matsuda, Y., Shibata, K., & Kasahara, K. (2020). Chemical pneumonitis caused by inhalation of white phosphorus fumes. American Journal of Respiratory and Critical Care Medicine, 201(4). https://doi.org/10.1164/rccm.201904-0734im (Year: 2020).*

Comeglio, et al: "Anti-fibrotic effects of chronic treatment with the selective FXR agonist obeticholic acid in the bleomycin-induced rat model of pulmonary fibrosis", Journal of Steroid Biochemistry & Molecular Biology, Apr. 2017, vol. 168, pp. 26-37, doi.org/10.1016/j.jsbmb.2017.01.010.

Fei, et al: "Obeticholic acid alleviate lipopolysaccharide-induced acute lung injury via its anti-inflammatory effects in mice", International Immunopharmacology, Jan. 2019, vol. 66, pp. 177-184, doi.org/10.1016/j.intimp.2018.11.005.

* cited by examiner

*Primary Examiner* — Kortney L. Klinkel
*Assistant Examiner* — Donna M Nestor
(74) *Attorney, Agent, or Firm* — FOX ROTHSCHILD LLP (57) ABSTRACT

A method of treating reduced pulmonary function by administering an effective dose of a Farnesoid X Receptor (FXR) agonist, particularly obeticholic acid, is disclosed. Also disclosed is an in vivo animal model of lung injury and altered functioning, useful for identifying compounds active in restoring pulmonary function.

20 Claims, 5 Drawing Sheets

Figure 7

PULMONARY FUNCTION TREATMENT

CROSS-REFERENCE TO RELATED APPLICATION

This application claims the benefit under 35 U.S.C. § 119(e) of U.S. Provisional Application No. 63/269,920, filed Mar. 25, 2022, the contents of which are incorporated herein in its entirety by reference thereto.

STATEMENT REGARDING FEDERALLY SPONSORED RESEARCH OR DEVELOPMENT

This invention was made with government support under grant numbers AR055073, DK126963, ES029258, ES033698, GM135258 awarded by the National Institutes of Health. The government has certain rights in the invention.

FIELD OF THE INVENTION

The present invention is related to the field of treatments for chemical injury to, or diseases of, the lungs where pulmonary function has been compromised, or is in the process of being compromised.

BACKGROUND

Various lung diseases are associated with reduced pulmonary function. Such diseases include asthma, emphysema, cystic fibrosis, autoimmune lung disease, and COVID-19. Various chemical agents can also attack the lungs, causing damage and reducing pulmonary function.

The Farnesoid X Receptor (FXR) is a nuclear receptor involved in bile acid and lipid homeostasis; it has also been shown to have anti-inflammatory activity. Located primarily in the ileum and liver, it has also been identified in the lungs, kidneys, adrenals and other tissues.

Effective treatments for ameliorating chemical injury to and/or diseases of the lungs represent an urgent need, particularly with regard to the ongoing COVID-19 pandemic. These types of lung diseases have traditionally been treated with oral medications (anti-inflammatory steroids, immunosuppressive drugs), oxygen therapy, pulmonary rehab, or lung transplant.

SUMMARY OF THE DISCLOSURE

It has now been discovered that FXR agonist compounds are effective treatments for patients suffering reduced pulmonary function resulting from chemical injury and lung disease. Described herein is a compound, obeticholic acid (OCA), which has been discovered to be effective in improving pulmonary function following chemical injury, and thereby is also expected to be effective in disease states including restrictive lung disease, asthma, emphysema, COPD, bronchiolitis obliterans, cystic fibrosis, autoimmune lung disease, constrictive bronchiolitis and COVID-19.

Figure 1:
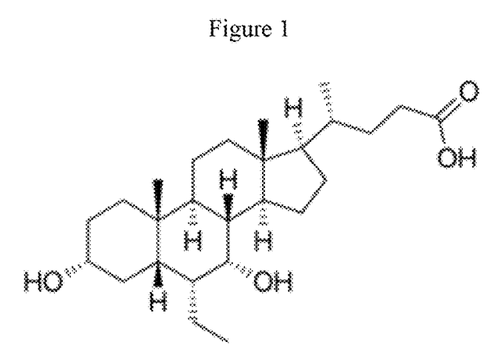
FIG. 1 displays the chemical structure of obeticholic acid (OCA).

Obeticholic acid (OCA), an FXR agonist, is a semi-synthetic compound with a similar structure to the endogenous bile acid chenodeoxycholic acid (CDCA). It is an FDA-approved drug sold under the brand name OCA-LIVA™, a semi-synthetic bile acid analogue which has the chemical structure 6α-ethyl-chenodeoxycholic acid; the structure is shown in FIG. 1. OCA is used as a medication to treat primary biliary cholangitis.

Other FXR agonist compounds are disclosed in S. M. W. van de Wiel et al., Scientific Reports, 9, 2193 (2019), "Identification of FDA-approved drugs targeting the Farnesoid X Receptor". Wikipedia identifies the following compounds to be FXR agonists: cafestol, chenodeoxycholic acid, fexaramine, GW 4064, ivermectin, obeticholic acid, and tropifexor.

One aspect of the invention is directed to a method of treating a subject with reduced pulmonary function, the method comprising administering an effective dose of an FXR agonist to a subject in need thereof for an effective period of time. Alternatively stated, the method of treating a subject with reduced pulmonary function administers a dose of an FXR agonist to a subject in need thereof, comprising an amount of the agonist that is effective to improve pulmonary function in the subject, and repeating administration of the FXR agonist for a period of time effective to at least partially restore pulmonary function.

In one embodiment, the FXR agonist is obeticholic acid or a pharmaceutically acceptable salt, solvate, or prodrug thereof. The reduced pulmonary function can result from chemical injury to the lungs. The chemical injury can result from exposure to a vesicant, including nitrogen mustard and sulfur mustard. Alternatively, the reduced pulmonary function can result from a disease. The disease can be restrictive lung disease, asthma, emphysema, COPD, bronchiolitis obliterans, cystic fibrosis, autoimmune lung disease, constrictive bronchiolitis or COVID-19.

Another aspect of the invention is directed to a method of treating diminished pulmonary function, the method comprising administering to a subject suffering from diminished pulmonary function, an amount of an FXR agonist composition effective to increase lung mechanics and improve oxygen/$CO_2$ exchange in the subject. In one embodiment the FXR agonist composition includes obeticholic acid, or a pharmaceutically acceptable salt or solvate thereof, and a pharmaceutically acceptable carrier or excipient.

The diminished pulmonary function can be due to the toxic effect of at least one of a vesicant and/or a highly toxic chemical. The highly toxic chemical can be selected from corrosive gases, strong acids, strong bases, dehydrating corrosives and corrosive solids. The vesicant can be selected from distilled mustard, mustard gas, lewisite, mustard/lewisite, mustard/T, nitrogen mustard, sesqui mustard, sulfur mustard, phosgene oxime and cantharidin. The corrosive gas can be selected from hydrogen sulfide, hydrogen fluoride, hydrogen chloride, hydrogen bromide, hydrogen cyanide, arsine, phosphine, nitric oxide, nitrogen dioxide, sulfur dioxide, ozone, chlorine, methylamine, and ammonia. The strong acid can be selected from the hydrochloric acid, sulfuric acid, and phosphoric acid. The strong base can be selected from sodium hydroxide, potassium hydroxide and aqueous ammonia. The strong dehydrating corrosive can be selected from concentrated sulfuric acid, phosphorous pentoxide and calcium oxide. The corrosive solid can be selected from phosphorous and phenol.

In the method of treating diminished pulmonary function, the effective amount of FXR agonist composition can be administered to the subject before the subject is exposed to a vesicant and/or a corrosive gas. Alternatively, the FXR agonist composition can be administered to the subject while the subject is being exposed to at least one of a vesicant and/or a corrosive gas. Alternatively, the FXR agonist composition can be administered to the subject after the subject has been exposed to at least one of a vesicant and/or a highly toxic chemical.

In the method of treating diminished pulmonary function, the toxic effect can be characterized by diminished pulmonary function induced by at least one of a vesicant and/or a highly toxic chemical. The effective amount of the FXR agonist composition can be administered to the subject by any one or more of an oral, intravenous, intramuscular, intracutaneous, subcutaneous injection, oral respiratory or nasal route. The diminished pulmonary function can be caused by the presence of lipid-laden foamy macrophages.

In any of the above methods, the effective amount of the FXR agonist can be about 1 to about 100 mg, or about 1 to about 75 mg, or about 1 to about 50 mg, or about 1 to about 25 mg. Alternatively the effective amount of the FXR agonist can be about 5 to about 90 mg, or about 10 to about 80 mg, or about 15 to about 70 mg, or about 20 to about 65 mg. The effective dose of the FXR agonist can be about 1 mg, or about 3 mg, or about 5 mg, or about 10 mg, or about 15 mg, or about 20 mg, or about 25 mg, or about 30 mg, or about 35 mg, or about 40 mg, or about 45 mg, or about 50 mg, or about 55 mg, or about 60 mg, or about 65 mg, or about 70 mg, or about 75 mg, or about 80 mg, or about 85 mg, or about 90 mg, or about 95 mg, or about 100 mg.

DETAILED DESCRIPTION

As disclosed herein, a number of ranges of values are provided. The recitation of numerical ranges by endpoints includes all numbers and fractions subsumed within that range, as well as the recited endpoints. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention. The term "about" generally includes up to plus or minus 10% of the indicated number. For example, "about 10%" may indicate a range of 9% to 11%, and "about 20" may mean from 18 to 22. Preferably "about" includes up to plus or minus 6% of the indicated value. Alternatively, "about" includes up to plus or minus 5% of the indicated value. Other meanings of "about" may be apparent from the context, such as rounding off, so, for example "about 1" may also mean from 0.5 to 1.4.

Unless otherwise defined, all terms used in disclosing the invention, including technical and scientific terms, have the meaning as commonly understood by one of ordinary skill in the art to which this invention belongs.

A "pharmaceutically acceptable salt" of a compound means a salt that is pharmaceutically acceptable and that possesses the desired pharmacological activity of the parent compound. It is understood that the pharmaceutically acceptable salts are non-toxic. Such salts include salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. Additional information on suitable pharmaceutically acceptable salts can be found in Remington's Pharmaceutical Sciences, 17th ed., Mack Publishing Company, Easton, PA, 1985, which is incorporated herein by reference.

Figure 2:
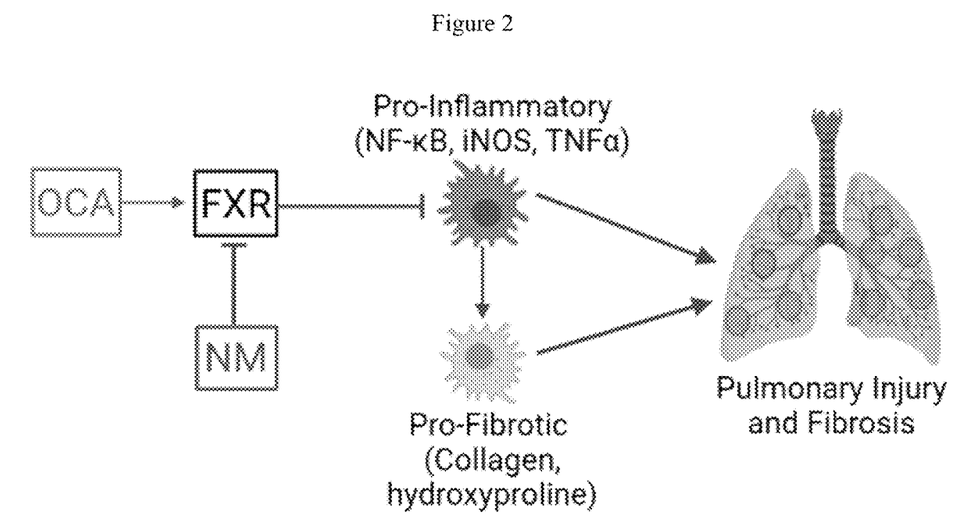
FIG. 2 is a schematic diagram showing the role of the Farnesoid X-receptor in the inflammatory process that results in pulmonary injury and fibrosis. OCA=obeticholic acid; FXR=Farnesoid X-receptor; NM=nitrogen mustard.

One aspect of the invention is directed to the use of obeticholic acid (OCA) to improve pulmonary function in patients with compromised lungs. OCA is an FDA-approved drug, under brand name OCALIVA™, for the treatment of primary biliary cholangitis. OCA acts by stimulating the activity of Farnesoid X Receptor (FXR), which is known to be involved in bile acid and lipid homeostasis and in suppressing inflammation. It has now been discovered that by activating FXR, OCA markedly improves pulmonary function in the damaged lungs of a rat model system; this is due to its ability to suppress the activity of pulmonary macrophages. See FIG. 2.

The efficacy of OCA as an FXR agonist has been tested in a rat model of lung injury and altered functioning induced by nitrogen mustard (NM). In this model, NM inhibits FXR from suppressing pro-inflammatory activity in the lung, leading to injury, pulmonary fibrosis, and alterations in pulmonary function.

Another aspect of the invention is the in vivo model system used to test the efficacy of OCA as a treatment to improve lung function in pulmonary compromised animals. This model is useful for identifying compounds active in restoring pulmonary function. This model was developed as follows.

In these studies, the progression of pulmonary injury was assessed following nitrogen mustard (NM) exposure and the role of OCA in regulating macrophage inflammatory activity, a major contributor to lung damage. Lung damage compromises pulmonary function. Male Wistar rats (n=35-40 rats/group) were exposed to phosphate-buffered saline (PBS, CTL) or NM (0.125 mg/kg) via i.t. Pencentury Microsprayer™ aerosolization. Following exposure, rats were treated orally with OCA (15 mg/kg/day) or vehicle control, 1x/day, 5 days/week. Lung tissue, bronchial alveolar lavage fluid, and alveolar macrophages (AMs) were collected 28 days post-exposure. NM-induced structural changes in the lung including septal-thickening, inflammatory cell infil-tration, pulmonary edema, and collagen deposition were significantly attenuated when treated with OCA. OCA markedly improved pulmonary function in NM treated animals. Analysis of hydroxyproline in tissue showed a 2-fold reduction in total collagen after treatment with OCA compared to NM alone. When analyzing protein expression and gene expression of inflamma-tory and oxidative stress markers (TNFα, NF-κB, HO-1, NOS2, pH2AX, IL-12) NM-induced increases were significantly reduced when treated with OCA. OCA also reduced NM-induced increases in SP-D, total phospholipids, and Oil Red O staining; these are classic lipid markers of inflammation. To confirm structural changes, the effects of NM and OCA on pulmonary function were assessed. NM reduced pulmonary resistance in the tissue indicating an emphysematous and fibrotic disease state; this was completely mitigated by OCA. Overall, these studies have shown that OCA reduces NM-induced pulmonary inflammation, oxidative stress, and fibrotic development. These findings indicate that OCA can improve structural and functional outcomes of progressive inflammatory disease in the lung.

In summary, one aspect of the invention is directed to a method of treating a subject with reduced pulmonary function, the method comprising administering an effective dose of an FXR agonist to a subject in need thereof for an effective period of time. In one embodiment the FXR agonist is obeticholic acid or a pharmaceutically acceptable salt, solvate, or prodrug thereof. The reduced pulmonary function can result from chemical injury to the lungs. The chemical injury can result from exposure to a nitrogen mustard. Alternatively, the reduced pulmonary function can result from a disease. The disease can be restrictive lung disease, asthma, emphysema, COPD, bronchiolitis obliterans, cystic fibrosis, autoimmune lung disease, constrictive bronchiolitis or COVID-19.

The effective dose or amount of the FXR agonist can range from about 1 to about 100 mg. The effective amount of the FXR agonist can be about 1 mg, or about 3 mg, or about 10 mg, or about 15 mg, or about 30 mg or about 100 mg.

EXAMPLES

The following examples are intended to be illustrative of the present invention, and in no way limit its scope.

Example 1

Figure 3:
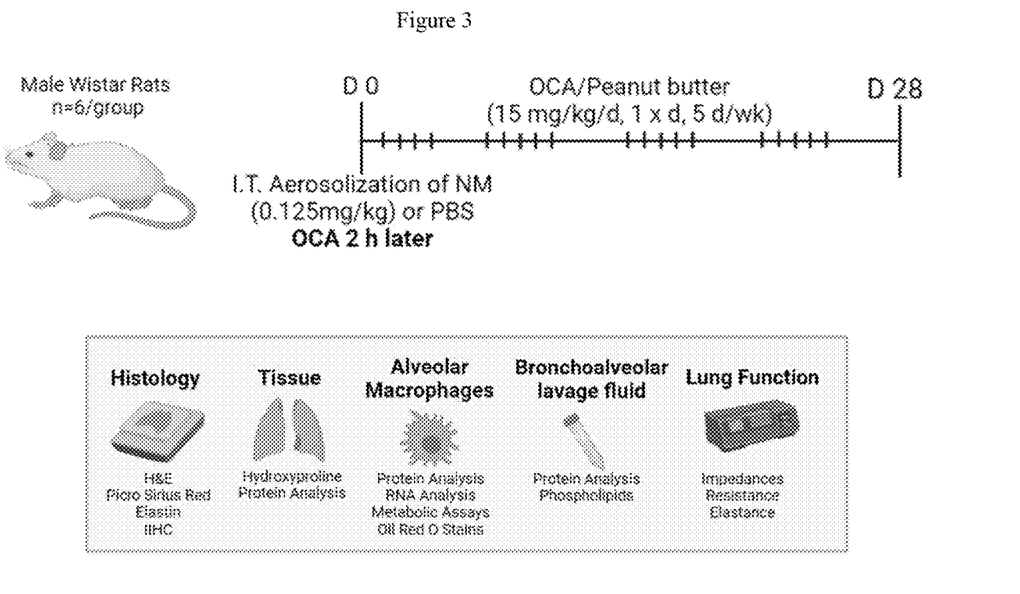
FIG. 3 is a schematic diagram of the experimental protocol.

Male Wistar rats were exposed to 0.125 mg/kg of the bifunctional alkylating agent nitrogen mustard (NM) through intratracheal aerosolization in the test group, or phosphate-buffered saline in the control group. After exposure, the rats were treated with 15 mg/kg of OCA or vehicle control once a day for 5 days a week. Lung tissue, alveolar lavage fluid, and lung functional parameters were assessed 28 days later. See FIG. 3 for a schematic diagram of the experimental protocol.

Figure 4:
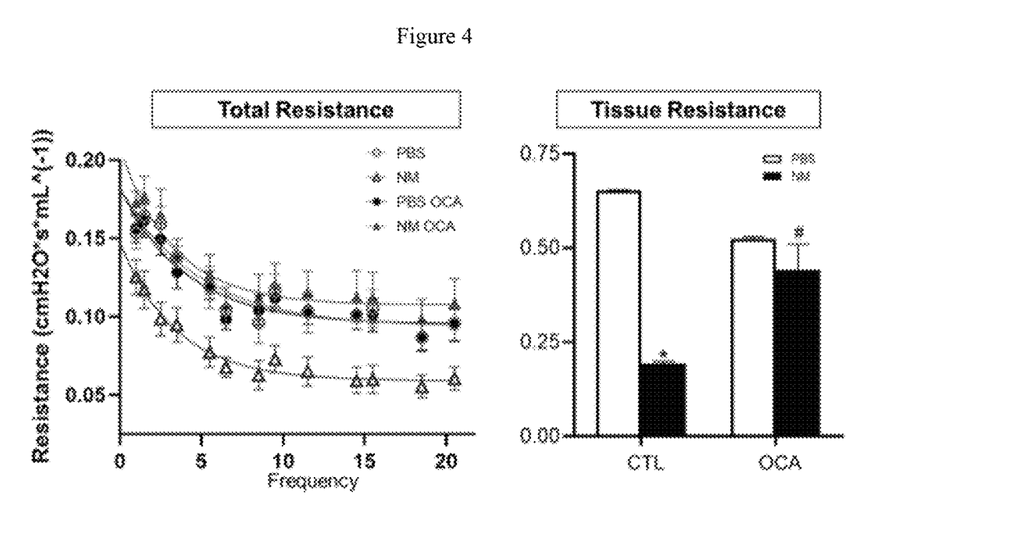
FIG. 4 compares graphs of the total resistance and tissue resistance for control (PBS, phosphate buffered saline) vs. chemical treatment (NM, nitrogen mustard), and response with subsequent OCA treatment. PEEP=positive end expiratory pressure, which is 3 mm $H_2O$ for the displayed graphs.

The effect of nitrogen mustard (NM) on pulmonary function (measured at positive end expiratory pressure of 3 mm $H_2O$) was shown to be mitigated by OCA. The treatment reduced NM-induced emphysematous-like increases in resistance of the lung tissue. Pulmonary function was normal in rats treated with both NM and OCA. See FIG. 4.

Figure 5:
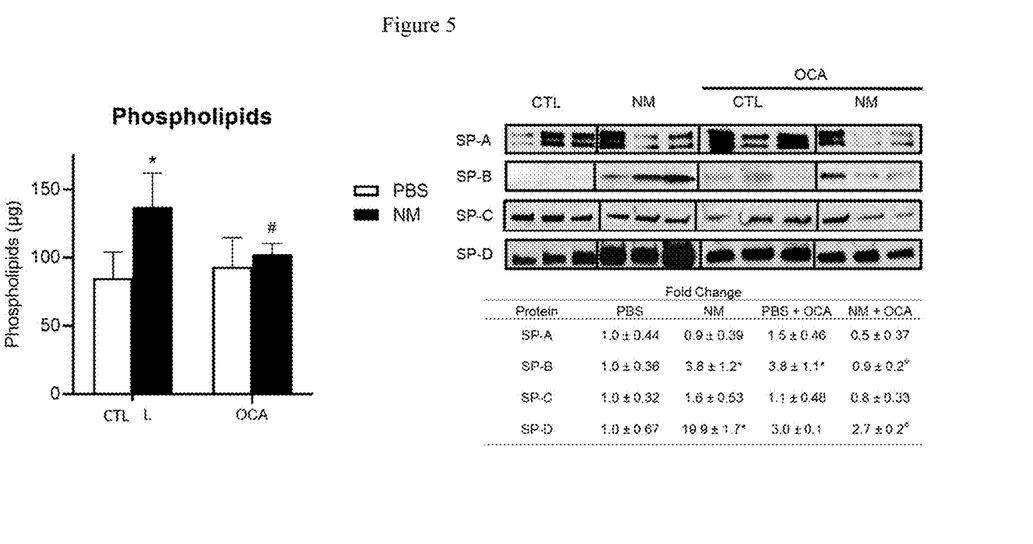
FIG. 5 displays graphs showing the effect of OCA treatment in reducing the dyslipidemia associated with NM-exposure. Specifically, NM increases total phospholipids and surfactant protein D expression in lung fluid and these are mitigated by OCA.
Figure 6:
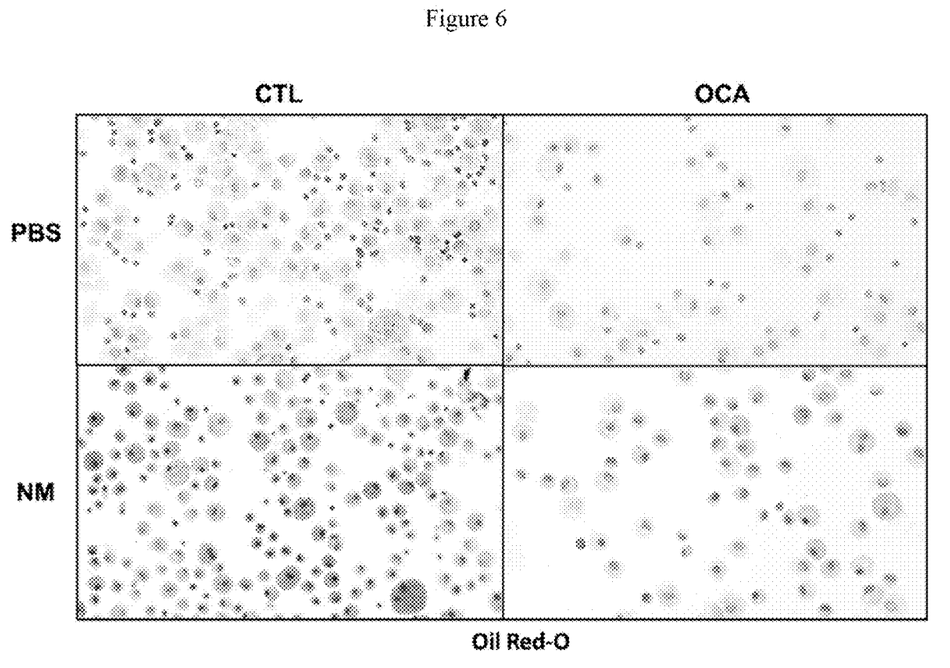
FIG. 6 shows lipid-laden foamy macrophages are increased following NM-exposure, indicated by staining with Oil Red 0. OCA blunts the appearance of these cells.

OCA was found to reduce nitrogen mustard (NM)-induced dyslipidemia, including total phospholipid and surfactant protein-D alterations; these markers are associated with altered lung function. See FIG. 5. Macrophages are known to be important in controlling lung function. Under conditions where the NM compromises pulmonary function and causes dyslipidemia, macrophages were found to increase lipid-laden foamy macrophages. These can be measured in cells using Oil Red 0 staining. Oil Red 0 is a lipid-soluble diazo dye. See FIG. 6.

Lipid-laden foamy macrophages can be the cause of a disease process not only in the lungs, but also in the liver, heart, bone marrow, gastrointestinal tract, kidneys, eyes, reproductive tract, adrenal and other endocrine glands, and brain.

Figure 7:
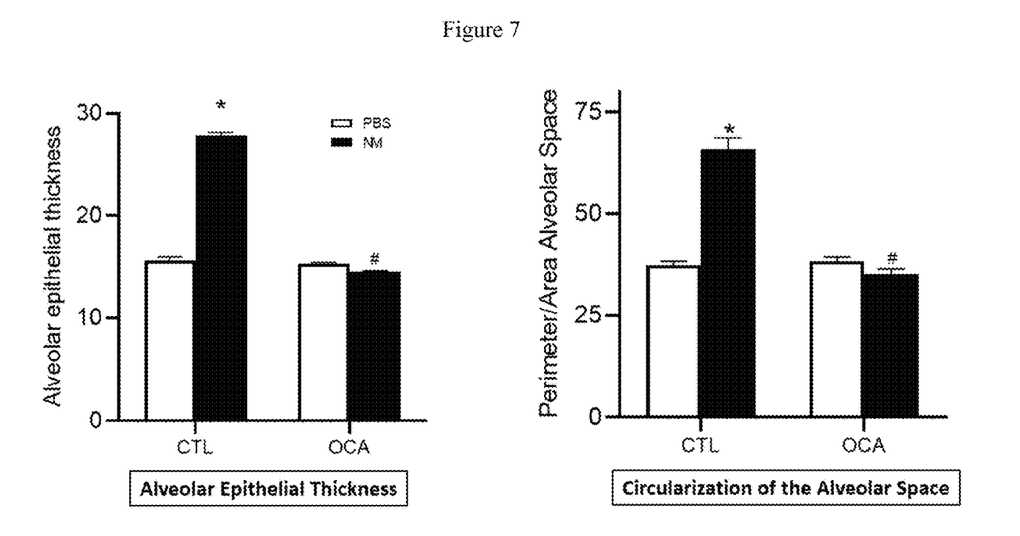
FIG. 7 displays graphs alveolar epithelial thickness and circularization of the alveolar space in for control (PBS, phosphate buffered saline) vs. chemical treatment (NM, nitrogen mustard), and response with subsequent OCA treatment.

OCA prevented structural changes in the alveoli caused by nitrogen mustard (NM); specifically, by reducing alveolar epithelial thickness associated with pulmonary fibrosis, and reducing alveolar circularization associated with emphysematous-like disease. See FIG. 7.

These results indicate that OCA, when administered at an effective dose for an effective period of time, would be useful for the treatment of diseases associated with reduced pulmonary function, such as restrictive lung disease, asthma, emphysema, cystic fibrosis, autoimmune lung disease, and COVID-19.

Example 2

Male Wistar rats were treated with PBS control, NM, OCA, or NM+OCA and lung function measured on a small animal ventilator. As above, rats were treated with NM to compromise pulmonary functioning. Animals were then treated with OCA (orally, 1x/day, 5 days per week). After 28 days, pulmonary function in the rats was determined using a small animal ventilator. It was found that NM decreased resistance of the lung tissue. It also decreased impedance, a measure of total pulmonary function including airway integrity. OCA was found to completely attenuate the effects of NM. Thus, animals treated with NM and OCA had normal pulmonary functioning. These data are important as it provides a route to treat patients with an agent where disease pathology compromises pulmonary function. Thus, there is the potential for OCA to be used in diseases such as restrictive lung disease, asthma, emphysema, bronchiolitis obliterans, cystic fibrosis, COVID-19, constrictive bronchiolitis and autoimmune lung disease.

It will be understood by those of skill in the art that numerous and various modifications can be made without departing from the spirit of the present invention. Therefore, it should be clearly understood that the various embodiments of the present invention described herein are illustrative only, and are not intended to limit the scope of the present invention.

What is claimed is:

1. A method of reducing alveolar epithelial wall thickening and improving pulmonary function in a patient suffering therefrom, the method comprising administering a dose of an Farsenoid X Receptor (FXR) agonist to said patient, comprising an amount of said agonist that is effective to reduce said alveolar epithelial wall thickening in said patient, wherein the FXR agonist is not an agonist for other receptors.

2. The method of claim 1, wherein the FXR agonist comprises obeticholic acid or a pharmaceutically acceptable salt, solvate, or prodrug thereof.

3. The method of claim 1, wherein the reduced pulmonary function results from chemical injury to the lungs.

4. The method of claim 3, wherein the chemical injury results from exposure to a nitrogen mustard or a sulfur mustard.

5. A method of reducing circularization of the alveolar space and improving pulmonary function in a patent suffering therefrom, the method comprising administering a dose of an FXR agonist to said patient subj-eet, wherein said dose is effective to reduce circularization of the alveolar space and increase lung mechanics and improve oxygen/CO2 exchange in said patient wherein the FXR agonist is not an agonist for other receptors.

6. The method of claim 5, wherein the FXR agonist composition comprises obeticholic acid, or a pharmaceutically acceptable salt or solvate thereof, and a pharmaceutically acceptable carrier or excipient.

7. The method of claim 5, wherein the diminished pulmonary function is due to the toxic effect of at least one of a vesicant and/or a highly toxic chemical.

8. The method of claim 7, wherein the highly toxic chemical is selected from corrosive gases, strong acids, strong bases, dehydrating corrosives and corrosive solids.

9. The method of claim 7, wherein the vesicant is selected from the group consisting of distilled mustard, mustard gas, lewisite, mustard/lewisite, mustard/T, nitrogen mustard, sesqui mustard, sulfur mustard, phosgene oxime and cantharidin.

10. The method of claim 8, wherein the corrosive gas is selected from the group consisting of hydrogen sulfide, hydrogen fluoride, hydrogen chloride, hydrogen bromide, hydrogen cyanide, arsine, phosphine, nitric oxide, nitrogen dioxide, sulfur dioxide, ozone, chlorine, methylamine, and ammonia.

11. The method of claim 8, wherein the strong acid is selected from the group consisting of hydrochloric acid, sulfuric acid, and phosphoric acid.

12. The method of claim 8, wherein the strong base is selected from the group consisting of sodium hydroxide, potassium hydroxide and aqueous ammonia.

13. The method of claim 8, wherein the strong dehydrating corrosive is selected from the group consisting of concentrated sulfuric acid, phosphorous pentoxide and calcium oxide.

14. The method of claim 8, wherein the corrosive solid is selected from phosphorous and phenol.

15. The method of claim 5, wherein the effective amount of FXR agonist composition is administered to the patient before or while the patient is exposed to a vesicant or a corrosive gas, or after the patient has been exposed to at least one of a vesicant and/or a corrosive gas.

16. The method of claim 5, wherein the toxic effect is characterized by diminished pulmonary function induced by at least one of a vesicant and/or a highly toxic chemical.

17. The method of claim 5, wherein the effective amount of the FXR agonist composition is administered to the patient by oral, intravenous, intramuscular, intracutaneous, subcutaneous injection, oral respiratory or nasal route.

18. The method of claim 5, wherein the effective amount of the FXR agonist is about 1 to about 100 mg.

19. The method of claim 1, wherein said alveolar epithelial wall thickening is not caused by a lung disease.

20. The method of claim 5, wherein said circularization of the alveolar space is not caused by a lung disease.

* * * * *

UNITED STATES PATENT AND TRADEMARK OFFICE
CERTIFICATE OF CORRECTION

PATENT NO. : 12,343,351 B2
APPLICATION NO. : 18/190680
DATED : July 1, 2025
INVENTOR(S) : Debra Lynn Laskin et al.

Page 1 of 1

It is certified that error appears in the above-identified patent and that said Letters Patent is hereby corrected as shown below:

In the Claims

At Column 7, Claim number 5, Line number 4 should read:
of an FXR agonist to said patient, wherein said dose Signed and Sealed this
Twenty-sixth Day of August, 2025

Coke Morgan Stewart
*Acting Director of the United States Patent and Trademark Office*